(12) United States Patent
Kapadia

(10) Patent No.: US 6,225,296 B1
(45) Date of Patent: May 1, 2001

(54) INHIBITORY EFFECTS OF SYNTHETIC AND NATURAL COLORANT ON CARCINOGENESIS VIII

(76) Inventor: Govind Kapadia, 8636 Red Coat La., Potomac, MD (US) 20854

(*) Notice: Subject to any disclaimer, the term of this patent is extended or adjusted under 35 U.S.C. 154(b) by 0 days.

(21) Appl. No.: 09/256,202

(22) Filed: Feb. 24, 1999

Related U.S. Application Data

(63) Continuation of application No. 08/845,166, filed on Apr. 21, 1997
(60) Provisional application No. 60/022,638, filed on Jul. 24, 1996.

(51) Int. Cl.[7] .................................................. A61K 31/18
(52) U.S. Cl. ............................. 514/150; 424/9.1; 514/166
(58) Field of Search ................................ 424/195.1, 9.1; 514/166, 150; 534/573, 583, 588, 599

(56) References Cited

U.S. PATENT DOCUMENTS 4,528,367 * 7/1985 Agback et al. ...................... 534/599
4,559,330 * 12/1985 Agback et al. ...................... 514/166

OTHER PUBLICATIONS

Survey of Compounds Which Have Been Tested for Carcinogenic Activity. Cumulative Indexes. National Cancer Institute. CCS Associates, Mountain View, CA. Mar. 1996.*

* cited by examiner

*Primary Examiner*—Robert H. Harrison
(74) *Attorney, Agent, or Firm*—Papan Devnani, Esq; C. C. Shroff

(57) ABSTRACT

A method of inhibiting Epstein-Barr virus early antigen induction in Epstein-Barr virus genome-carrying cells which have been cultivated in vitro in a medium containing at least one chemical selected from the group consisting of tumor-inducing chemicals and tumor promoting chemicals by adding an effective amount of a synthetic colorant to the medium, wherein the synthetic colorant is an aromatic azo dye.

23 Claims, 6 Drawing Sheets

INHIBITORY EFFECTS OF SYNTHETIC AND NATURAL COLORANT ON CARCINOGENESIS VIII

This application claims the benefit of U.S. Provisional Application No. 60/022,638, filed Jul. 24, 1996, and of U.S. application Ser. No. 08/845,166, filed Apr. 21, 1997.

FIELD OF THE INVENTION

The field of the invention relates to use of food colorants in the treatment or prevention of cancer. More particularly, the invention relates to use of safe, nontoxic food colorants to inhibit carcinogenesis. The food colorants may be natural pigments extracted from a plant or plants, or they may be synthetic compounds approved by the FDA for use as food colorants or food dyes.

BACKGROUND OF THE INVENTION

A wide variety of colorants have been approved by the FDA for use in foods, pharmaceuticals, and cosmetic preparations. Extensive toxicity studies have been performed on each of these compounds, and they have been found to be nontoxic. However, relatively little research has been performed to determine whether use of these colorants in foods, drugs, and cosmetics is actually beneficial, rather than simply not harmful.

We have been conducting studies designed to help fill this gap. Our research is directed towards use of natural and synthetic food colorants in the inhibition of carcinogenesis. In past work, we have described inhibition of tumor formation by natural colorants and extracts of fruits, vegetables, and other plant parts (Kapadia et al., *Proc. Int Congress on Nat. Prod. Research,* Abstract No. 225; Halifax, Canada; 1994). Extracts of turmeric, paprika, and annatto seeds have been found to be of great interest, particularly in the prevention of cancer. Paprika extracts, obtained from *Capsicum annum L.* (Fam: Solanacaea), are among the oldest and most important carotenoid extracts. The main carotenoids present in paprika are capsanthin (I) and capsorubin (II), largely as their acyl esters. Other minor components are present.

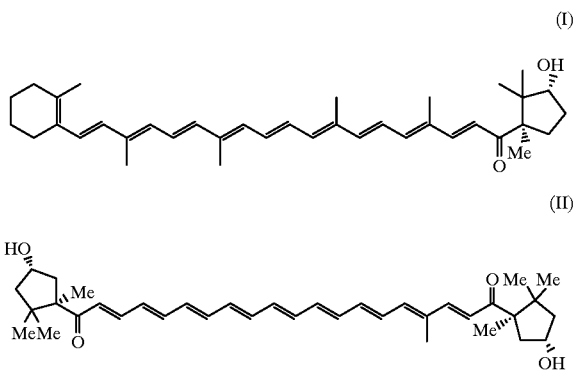

(I)

(II)

Annatto seeds are the seeds of the tropical bush *Bixa orellana L.* (Family: Bixaceae). The major pigment is the carotenoid cis-bixin (III), the monomethyl ester of diapocarotenoic acid (IV; also known as cis-norbixin). Trans-bixin and cis-norbixin are also present as minor constituents. Trans-bixin and cis-bixin are both sparingly water-soluble, and may be converted to a water-soluble salt of the corresponding norbixin upon alkali hydrolysis.

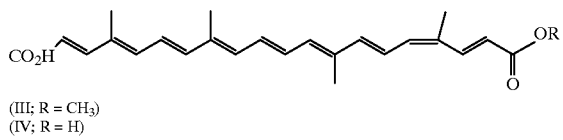

(III; R = CH₃)
(IV; R = H)

Turmeric, also called curcuma, is a fluorescent yellow-colored extract from the rhizomes of several species of the curcuma plant. *Curcuma longa* is the usual commercial source. The pigments curcumin (V), demethoxycurcumin (VI), and bisdemethoxycurcumin (VII) occur in every species, together with mirror ingredients that contribute to the flavor.

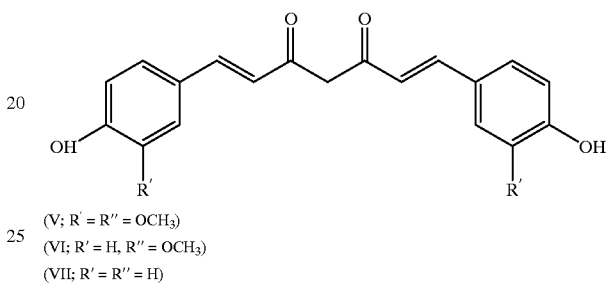

(V; R' = R'' = OCH₃)
(VI; R' = H, R'' = OCH₃)
(VII; R' = R'' = H)

Other natural colorants that have been found to be of interest include the betanins and the anthocyanins. Betanins may be readily extracted from beet roots, and anthocyanins may be extracted from grapes, red onion skin, cranberries, and other plant-derived materials.

The studies reported herein include in vitro studies of inhibition of Epstein-Barr virus early antigen (EBV-EA) induction studies by synthetic colorants and by natural plant extracts and colorants. The Epstein-Barr virus (EBV) is a member of the herpes virus family, and has been implicated in the pathogenesis of Burkitt's lymphoma, nasopharyngeal carcinoma, and B lymphocyte neoplasms. Infection of a human by EBV is commonly followed by a latency period, when the virus is present intracellularly in an unexpressed state. T cell suppressor mechanisms of the immune response to EBV are effective in the inhibition of acute EBV infection. If these mechanisms fail, Burkett's lymphoma, nasopharyngeal carcinoma, and B cell lymphomas may emerge. This is a serious problem during the postoperative recuperation period following organ transplants, as immunosuppresive therapy is often used to prevent rejection. It is therefore important to find new cancer chemopreventive agents which prevent formation of tumors linked to the Epstein-Barr virus. In vitro inhibition of EBV-EA induction in Epstein-Barr virus genome-carrying cells by a potential cancer chemopreventive compound serves as an excellent sign that the compound may inhibit tumor formation in a living organism. In fact, inhibitory activity toward EBV-EA induction is often taken as a measure of anti-tumor promoting activity.

In vivo studies of inhibition of skin tumor formation by synthetic and natural colorants were also performed, using a two-stage mouse skin carcinogenesis test. A diagram illustrating such a test is provided in FIG. 1. Studies on rats and mice provide insight into the cancer induction process in humans and animals. Two mice (or groups of mice) are each treated with a compound known to initiate tumor formation (stage 1). In FIG. 1, 7,12-dimethylbenz[a]anthracene (DMBA) is used as the tumor initiator; other compounds may be used. The mice are then subjected to a condition or compound on a continued basis that promotes tumor formation (stage 2). Ultraviolet B radiation serves as an effective tumor promoter, as shown in FIG. 1. Topical application of 12-O-tetradecanoylphorbol-13-acetate (TPA) also serves as a promoter of skin tumors. One animal, the test animal, is provided an inhibitor of tumor promotion. The inhibitor may be provided in drinking water or topically applied to the skin. The other animal, the control animal, is provided with no inhibitor. At the end of a defined period, the number of tumors on the test animal is compared to the number of tumors on the control animal. Similar tests were performed for inhibition of pulmonary tumor formation, using injected 4-nitroquinoline 1-oxide as a tumor initiator and glycerol, provided in drinking water as a tumor promoter.

In *EMF Health Report,* vol. 1, No. 2 (1993), cancer initiators are defined as compounds that cause genetic damage. Only a single exposure is required to start the cancer-forming process. Compounds which initiate tumor formation include nitrosamines, alkylating agents, aromatic amines, polycyclic aromatic hydrocarbons, dimethylbenz [□]anthracene, vinyl chloride, asbestos, N-methyl-N-nitrosourea, and azaserine, as disclosed in *Advances in Cancer Research,* vol. 50, pp. 26–30.

In *EMF Health Report,* vol. 1, No. 2 (1993), cancer promoters are defined as compounds that cause irritation, inflammation, and cell growth when applied to an animal alone, and which increase the rate of tumor growth when applied after exposure to an initiator. Compounds which initiate tumor formation include active phorbol esters, such as tetradecanoylphorbol acetate and phorbol dibenzoate; teleocidin and related compounds; aplysiatoxin and related compounds; mezerein; tetradecanoyl ingenol; iodoacetic acid; benzoyl peroxide; palytoxin; and anthralin. These promoters are disclosed in *Biomedicine & Pharmacotherapy,* vol. 42, pp. 447–450, and in *Advances in Cancer Research,* vol. 50, pp. 26–30 (1987).

The phrases "chemical substance selected from the group consisting of tumor promoters and tumor initiators" is intended to encompass those compounds specifically named in Exhibits B–D. Those compounds which fall under the definitions provided in *EMF Health Report,* vol. 1, No. 2 (1993), and which a worker of ordinary skill in the art would have known to be a functional equivalent of a phorbol ester tumor promoter or a dimethylbenz[□]anthracene tumor promoter, are also included.

SUMMARY OF THE INVENTION

A first object of this invention is to evaluate a series of FDA-approved synthetic food colorants for inhibitory effects on carcinogenesis. The colorants were tested using in vitro assays for inhibition of Epstein-Barr virus early antigen (EBV-EA) induction in cells exposed to the tumor promoter 12-O-tetradecanoylphorbol-13-acetate (TPA). High inhibitory activity toward EBV-EA induction is known to be indicative that a composition has potential utility as an anti-tumor promoting or cancer chemopreventive agent. Epstein-Barr virus genome-carrying lymphoblastoid cells (Raji cells) were used in the in vitro studies.

Synthetic food colorants which were found to be particularly effective as inhibitors of EBV-EA induction include:

a) sulfonated azo compounds having formula VIII:

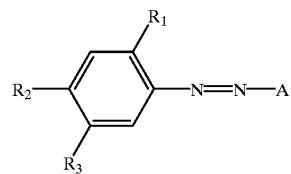

(VIII)

wherein A is

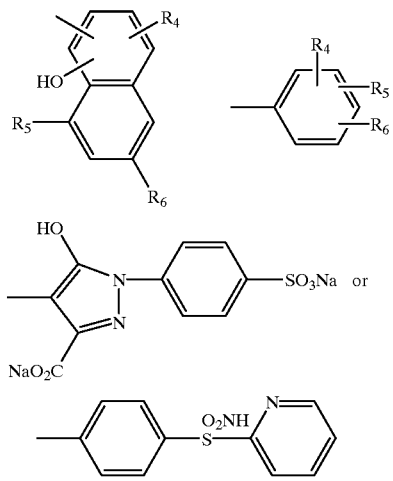

and wherein $R_1$ is —H, lower alkyl, lower alkoxy, —$CO_2H$, or —$SO_3M$; $R_2$ is —H, lower alkyl, or —$SO_3M$; $R_3$ is —H, lower alkyl, or —$SO_3M$; $R_4$ is —H, —$CO_2M$, or —$SO_3M$; $R_5$ and $R_6$, which may be the same or different, are independently selected from the group consisting of —H, —OH, —$NL_2$, —$CO_2M$, or —$SO_3M$; L is —H, lower alkyl, or lower hydroxyalkyl, and M is —H, an alkali metal cation, or an alkaline earth metal cation;

b) colorants of formula IX and alum lake colorants derived from colorants of formula IX:

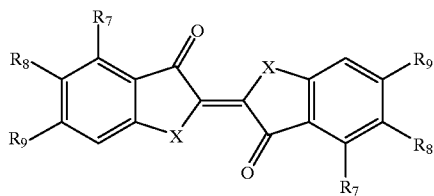

(IX)

wherein X is —NH— or —S—, $R_7$ is —H or lower alkyl; $R_8$ is —H or —$SO_3M$; $R_9$ is —H or —Cl; and M is —H or an alkali metal cation;

c) colorants of formula X:

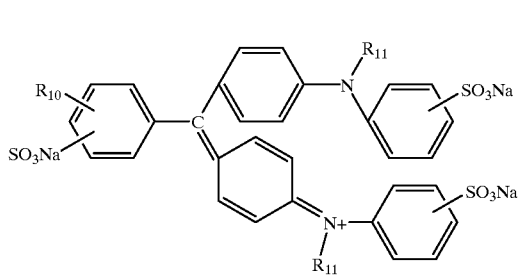

wherein $R_{10}$ is —H or —OH and each $R_{11}$ is a lower alkyl group;

d) fluorescein derivatives of formula XI:

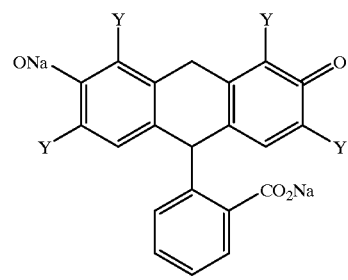

wherein Y is —H or —Br; and fluorescein derivatives of formula XII:

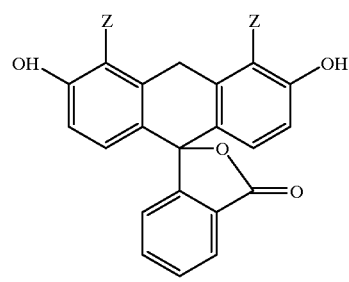

wherein Z is —H, —Br, or —I;

e) anthroquinone derivatives including dyes of formula XIII:

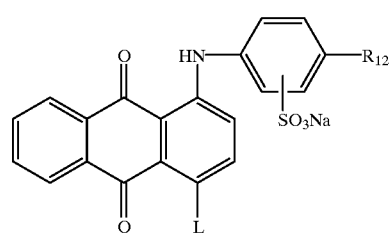

wherein $R_{12}$ is —H or lower alkyl and L is —OH or

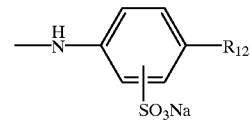

carmine (XIV); and carminic acid (XV);

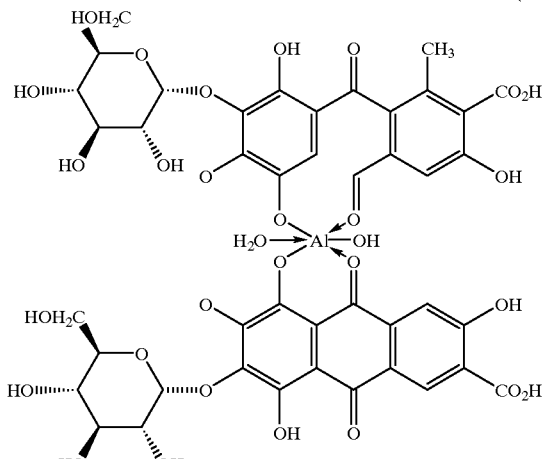

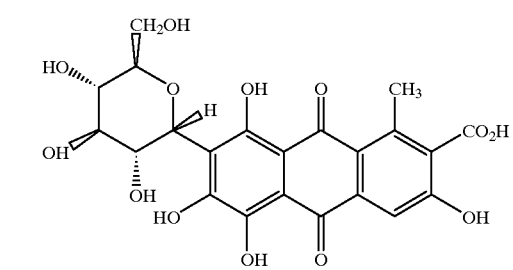

and f) a pyrene derivative of formula XVI:

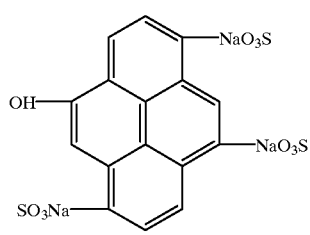

Although other synthetic colorants were effective as well, aromatic azo compounds, or azo dyes, which contain acidic or anionic groups appear to be of particular utility in inhibition of carcinogenesis. Some of the synthetic colorants which exhibited measurable inhibition of EBV-EA induction were then bioassayed to determine whether they inhibited TPA-promoted carcinogenesis in epidermal tissue. It was found that the colorants which were tested in the bioassay appear to measurably inhibit formation of chemically-promoted skin tumors.

A second object of the invention is to evaluate a series of plant extracts for inhibitory effects on carcinogenesis. The in vitro inhibitory effects of beet root extract and of grape extract on Epstein-Barr virus early antigen induction in Raji cells exposed to the tumor promoter TPA were assayed, and found to show significant anti-tumor promoting activity. In fact, the inhibitory activity of beet root extract was found to be greater than that shown by extracts of red bell peppers, red onion skin, paprika, and cranberries. In vivo studies of carcinogenesis inhibition by beet root extract were then performed. When beet root extract was given orally to mice, formation of skin tumors promoted by topical application of TPA or by exposure to UV radiation was significantly reduced. Also, beet root extract given orally reduced the incidence of glycerol-promoted pulmonary tumor formation.

Research was also done on natural food colorants extracted from turmeric, annatto seeds, and paprika. These colorants are commercially available in a variety of formulations in aqueous, vegetable oil, or propylene glycol vehicles. These vehicles may also contain emulsifiers and/or dispersants such as polysorbate 80 and lecithin. Recent studies have reported that colorants derived from turmeric, annatto, and paprika inhibit carcinogenesis. In the work described herein, the anti-tumor promoting activity of over thirty natural colorant formulations was investigated. Many of these formulations were found to exhibit significant in vitro inhibition of EBV-EA activation in Raji cells. However, many of these formulations exhibited cytotoxicity, suggesting that use of these compositions to inhibit tumor formation may pose hazards to human health. Fortunately, some compositions which in inhibited EBV-EA activation without exhibiting cytotoxicity were identified. The most effective of these compositions were;

a) a mixture of natural extractives of annatto seeds and turmeric with polysorbate 80, potassium hydroxide, and propylene glycol; and b) a natural extractive of paprika in vegetable oil.

In vivo studies indicate that oral feeding of paprika and annatto extracts acts to inhibit TPA-induced skin tumor formation. They were also found to be effective anti-inflammatory agents.

DETAILED DESCRIPTION OF THE INVENTION

Figure 1:
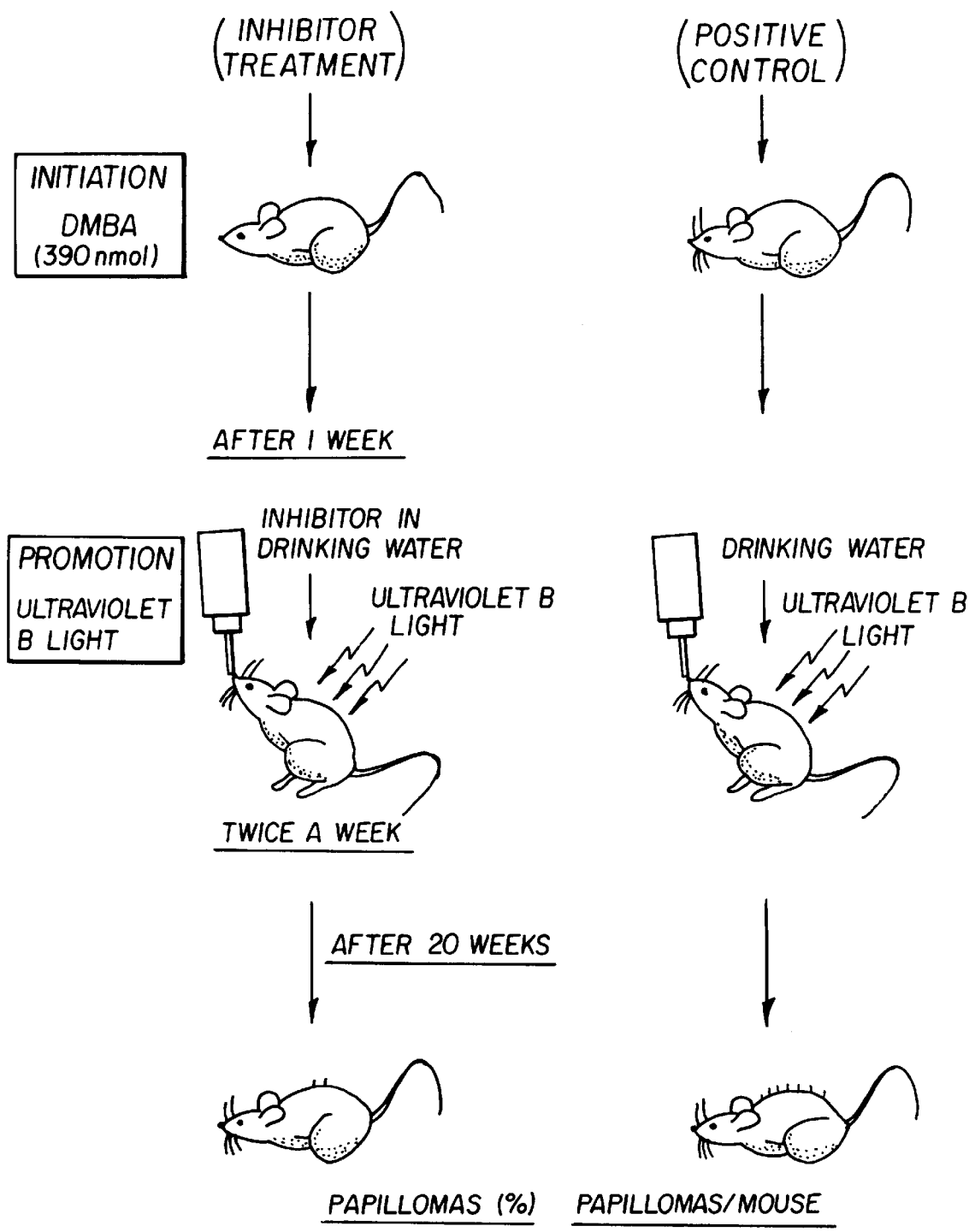
FIG. 1 illustrates the method used to perform a bioassay for anti-tumor promoting activity using a two-stage mouse skin carcinogenesis test.

1. In Vitro Studies on Inhibition of EBV-EA Activation
   1.1 Materials and Methods In vitro studies were carried out using an Epstein-Barr virus (EBV) early antigen induction assay performed in the following manner. EBV genome-carrying lymphoblastoid cells (Raji cells) were cultivated in an RMPI 1640 medium. The indicator cells were incubated at 37° C. for 48 hours in 1 ml of the medium. The medium also contained the tumor promoter TPA (20 ng/ml, or 32 pM), the tumor co-inducer butyric acid (4 mM), and a known amount of test dye in dimethylsulfoxide (DMSO). Smears were then made from the cultured cell suspension. The cells exhibiting EBV activation in each smear were stained by high titer EBV-positive sera from nasopharyngeal carcinoma patients and detected using conventional indirect immunofluorescence techniques. In each assay, at least 500 cells were counted and the experiments were repeated at least twice. The average EA induction of each assay was compared to that of a positive control experiment. In the control experiment, Raji cells were incubated at 37° C. for 48 hours in 1 ml of the medium. The medium also contained the tumor promoter TPA (20 ng/ml, or 32 pM) and the tumor co-inducer butyric acid (4 mM). In the control experiments, EA induction was normally around 30%.

In order to determine whether or not the synthetic colorants tested in the EBV-EA activation tests exhibited unacceptable cytotoxicity, cell viability tests were performed using the trypan-blue staining method. After the EBV-EA activation test, 0.1 ml of a suspension of treated cells from the EA induction test in phosphate buffer solution was stained with 0.1 ml of a 0.25% trypan-blue solution. Dying cells were dyed blue. Non-dyed cells were counted. If more than 40% of cells were dyed blue (that is, fewer than 60% of the cells were living, viable cells), the cytotoxicity of the test compound used in the EA induction test was judged to be unacceptably high.

The synthetic colorants which were tested for inhibition of EBV-EA induction using the assay techniques described above were obtained as gifts from the following sources:

a) Dr. A. Weiss
Food and Drug Administration
Center for Food Safety and Applied Nutrition
Office of Cosmetics and Colors
Washington, D.C.

b) Crompton and Knowles Corp.
Mahwah, N.J.

c) Hilton Davis Co.
Cincinnati, Ohio d) Pylam Products Co., Inc.
Garden City, N.Y.

The plant-derived colorant formulations which were tested for inhibition of EBV-EA activation by the described techniques are listed in Tables 1 and 2. Table 1 lists colorant compositions derived from vegetable extracts, including beet roots, bell peppers, and onion skin. Table 2 lists a series of colorant formulations derived from turmeric, annatto seeds, and/or paprika, together with some purified pigments which were tested for comparison. Curcumin and the colorant formulations derived from turmeric, annatto seeds, and/or paprika were made available to us as gifts from Kalsec, Inc., Kalamazoo, Mich. Bixin, capsanthin, and beetroot extract (betanin) were purchased from Tokyo Kasei Co., Japan through TCI America, Portland, Oreg., USA. Grape extract was supplied by Penta Manufacturing, a division of Penta International Corporation, Fairfield, N.J. Beetroot extract (betanin), grape extract, and capsanthin (derived from paprika) were used without further processing. Red onions, cranberries, long red bell peppers (12 cm long, 7 cm wide at the top, and 5 cm wide at the bottom), short red bell peppers (10 cm long, 7 cm wide at the top, and 4.5 cm wide at the bottom), purple bell peppers, green bell peppers, and light yellow green bell peppers were purchased at a supermarket in Potomac, Md. and used to prepare extracts.

To prepare extracts, the dry skin of onion and the other plant materials (cranberries, long red bell peppers, short red bell peppers, purple bell peppers, green bell peppers, and light yellow green bell peppers) were separately crushed in a blender. In each case, a weighed amount of material was mechanically shaken in a 250 ml flask for 1 hr with 95% ethanol. The mixture was thereafter centrifuged and the supernatant was decanted and filtered. The insoluble residual material was twice reextracted for 20 min by stirring with half the volume of the same solvent as used during the first extraction. The combined extracts were evaporated under a vacuum and weighed, and the percentage yields were recorded. The yield of the dry red onion skin alcoholic extract was 13.2%; that from cranberry was 7.06%; from short red bell pepper 7.06%; and from long red bell pepper 10%.

7,12-dimethylbenz(□)anthracene, acetone, phenobarbitol, and N-nitrosodiethylamine (DEN) were purchased from Wako Pure Chemical Industries, Osaka, Japan. (E)-4-methyl-2-[(E)-hydroxyamino]-5-nitro-6-methoxy-3-hexenamide (NOR1) was purchased from Dojindo Laboratories, Kumamoto, Japan.

TABLE 1

Vegetable-Derived Colorant Extracts Tested for EBV-EA Inhibition

| Extract | Colorant Ingredient |
|---|---|
| Beet Root | Betanins |
| Red Onion Skin | Anthocyanins |
| Paprika | Capsanthin |
| Cranberry | Anthocyanins |
| Short Red Bell Peppers | Carotenoids |
| Long Red Bell Peppers | Carotenoids |
| Grape | Anthocyanins |

TABLE 2

Turmeric-, Paprika-, and/or Annatto Seed-Derived Colorant Formulations Tested for EBV-EA Inhibition

| Colorant Formulation No. | Composition (As provided in the product literature) |
|---|---|
| 1 | Turmeric, Curcumin Content 85–97% |
| 2 | Turmeric, Curcumin Content 29–31% |
| 3 | Natural Extractives of Turmeric with not more than 80% Polysorbate 80, KOH, and Antifoam |
| 4 | Natural Extractives of Annatto Seeds and Turmeric with Polysorbate 80, KOH, and Propylene Glycol |
| 5 | Natural Extractives of Annatto Seeds and Turmeric with Vegetable Oil and Fumed Silicon Dioxide |
| 6 | Natural Extractives of Annatto Seeds and Turmeric with Vegetable Oil, Mono-, Di-, and Triglycerides, 7.3% BHT, and Fumed Silicon Dioxide |
| 7 | Natural Extractives of Turmeric and Paprika with Vegetabie Oil and Fumed Silicon Dioxide |
| 8 | Natural Extractives of Annatto Seeds with Water and KOH with Norbixin Content of 1.04–1.16% |
| 9 | Extractives of Annatto Seeds with Water and KOH with Norbixin Content of 2.6–2.8% |
| 10 | Extractives of Annatto Seeds with Propylene Glycol and KOH with Bixin Content of 2.48–2.67% |
| 11 | Natural Extractives of Turmeric with Lecithin, Mono- and Diglycerides, and Vegetable Oil |
| 12 | Natural Extractives of Annatto Seeds and Turmeric with Polysorbate 80, KOH, and Propylene Glycol |
| 13 | Natural Extractives of Annatto Seeds with Vegetable Oil |
| 14 | Natural Extractives of Annatto Seeds with Vegetabie Oil, Mono-, Di-, and Triglycerides, and KOH |
| 15 | Natural Extractives of Annatto Seeds with PropyleneGlycol, Water, and KOH |
| 16 | Natural Extractives of Annatto Seeds and Turmeric with Vegetable Oil and Fumed Silicon Dioxide |
| 17 | Natural Extractives of Annatto Seeds with Propylene Glycol, Polysorbate 80, and KOH with Bixin Content of 2.48–2.67% |
| 18 | Natural Extractives of Turmeric with Mono-, Di-, and Triglycerides, and Propylene Glycol |
| 19 | Natural Extractives of Paprika and Turmeric with Vegetable Oil and Fumed Silicon Dioxide |
| 20 | Natural Extractives of Turmeric with Propylene Glycol |
| 21 | Natural Extractives of Paprika with Vegetable Oil |
| 22 | Natural Extractives of Annatto Seeds with Vegetable Oil |
| 23 | Natural Extractives of Paprika with Mono- and Di-glycerides, Lecithin, and Vegetable Oil |
| 24 | Natural Extractives of Turmeric with Polysorbate 80 |
| 25 | Natural Extractives of Annatto Seeds and Turmeric with Vegetable Oil |
| 26 | Natural Extractives of Annatto Seeds and Paprika with Vegetable Oil and Fumed Silicon Dioxide |
| 27 | Natural Extractives of Turmeric with Vegetable Oil |
| 28 | Natural Extractives of Annatto Seeds with Vegetable Oil and Fumed Silicon Dioxide |
| 29 | Natural Extractives of Annatto Seeds with Water and KOH |
| 30 | Natural Extractives of Annatto Seeds with Vegetable Oil, Mono- and Di-glycerides and Lecithin |
| 31 | Natural Extractives of Annatto Seeds with Propylene Glycol, Water and KOH |
| 32 | Natural Extractives of Annatto Seeds with Water and KOH with Norbixin Content of 3.65–4.0% |
| 33 | Natural Extractives of Annatto Seeds with Vegetable Oil, Mono-, Di-, and Triglycerides, and KOH |
| 34 | Natural Extractives of Annatto Seeds and Paprika with Vegetable Oil, Mono-, Di-, and Triglycerides, and KOH |
| 35 | Natural Extractives of Annatto Seeds and Turmeric with Polysorbate 80, KOH, and Propylene Glycol |
| 36 | Bixin/Annatto Extract |
| 37 | Capsinthin/Paprika Extract in Vegetable Oil |

1.2 Results and Discussion

A wide variety of synthetic colorants were tested for in vitro inhibition of Epstein-Barr virus early antigen induction by TPA. The tested synthetic colorants include:

a) the following aromatic azo compounds:
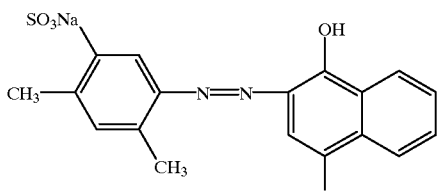
FD&C Red #4 (XVII)
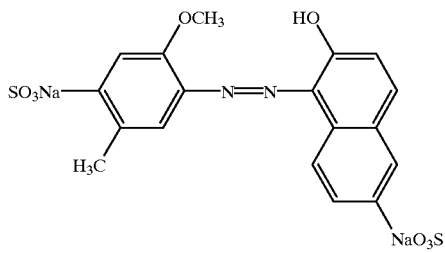
FD&C Red #40 (XVIII)
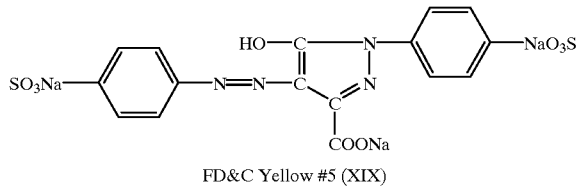
FD&C Yellow #5 (XIX)
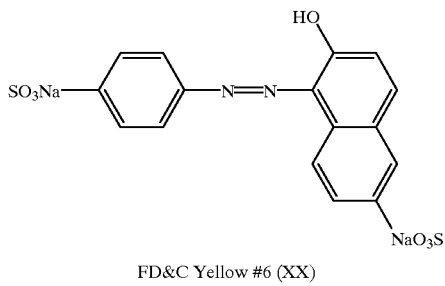
FD&C Yellow #6 (XX)
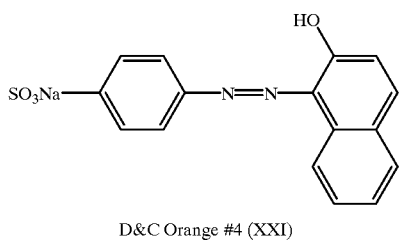
D&C Orange #4 (XXI)
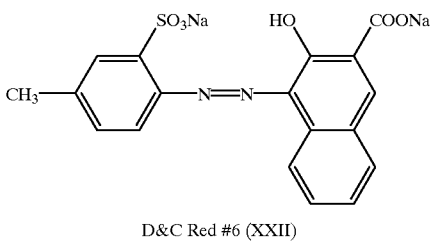
D&C Red #6 (XXII)
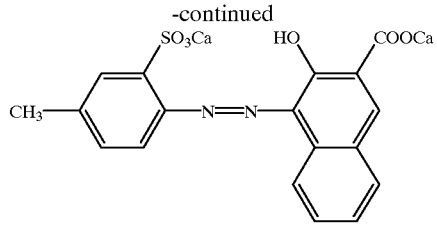
D&C Red #7 (XXIII)
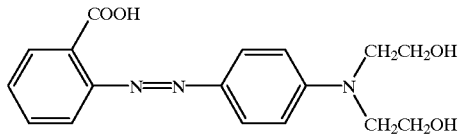
D&C Red #39 (XXIV)
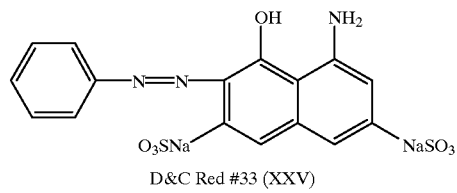
D&C Red #33 (XXV)
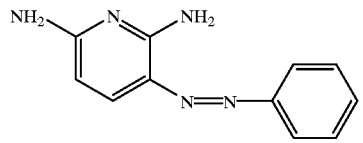
Phenazopyridine hydrochloride
(Phenazo; XXVI)
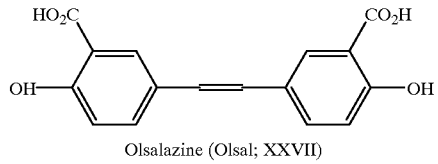
Olsalazine (Olsal; XXVII)
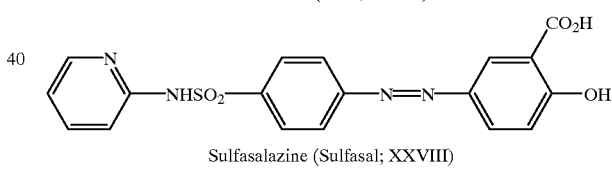
Sulfasalazine (Sulfasal; XXVIII)
b) indigo and the following related compounds:
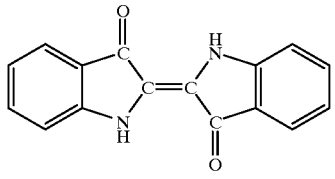
FD&C Blue #6 (XXIX)
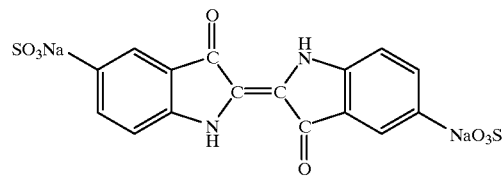
D&C Blue #2 (XXX)

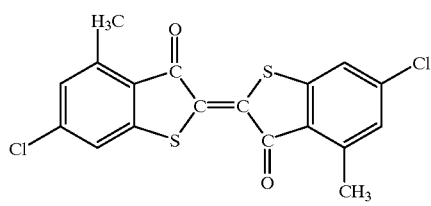
D&C Red #30 (XXXI)
c) the following substituted triphenylmethyl compounds:
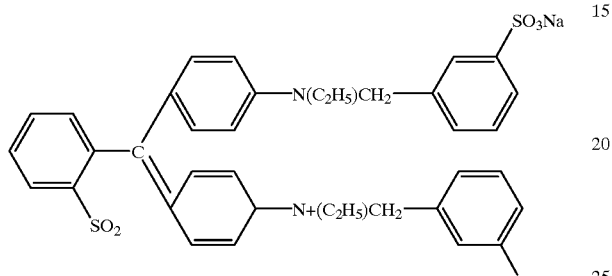
FD&C Blue #1 (XXXII)
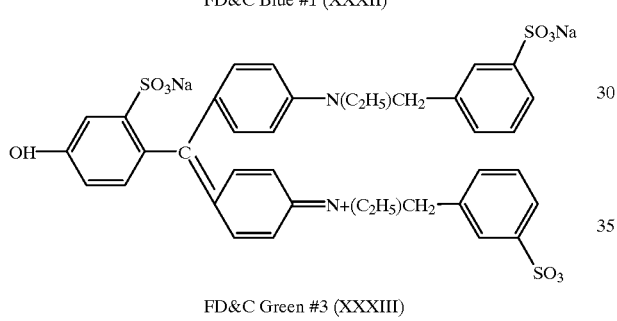
FD&C Green #3 (XXXIII)
d) the following substituted fluorescein compounds:
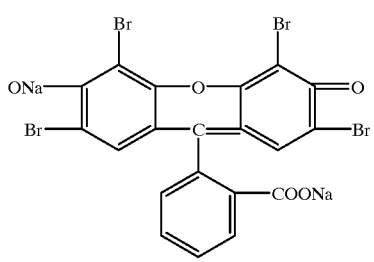
D&C Red #22 (XXXIV)
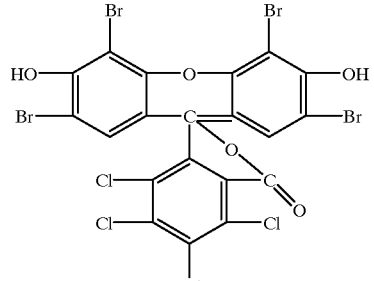
D&C Red #27 (XXXV)
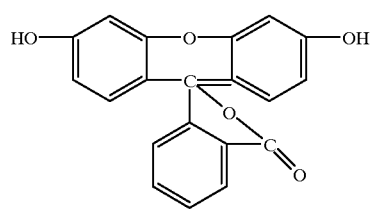
D&C Yellow #7 (XXXVI)
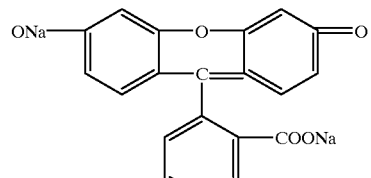
D&C Yellow #8 (XXXVII)
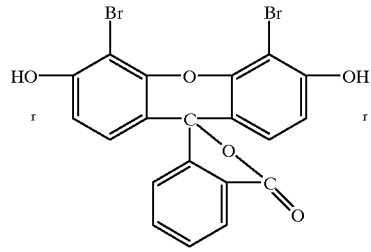
D&C Orange #5 (XXXVIII)
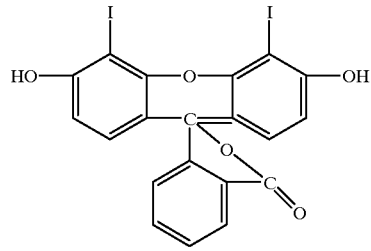
D&C Orange #10 (XXXIX)
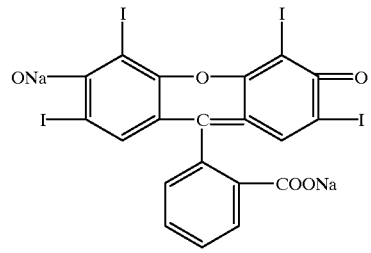
FD&C Red #3 (XXXX)
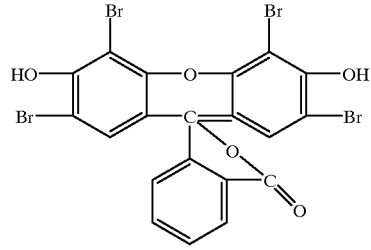
D&C Red #21 (XXXXI)

-continued

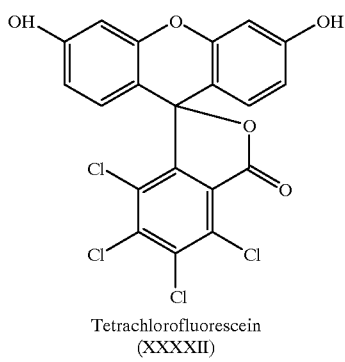

Tetrachlorofluorescein
(XXXXII)

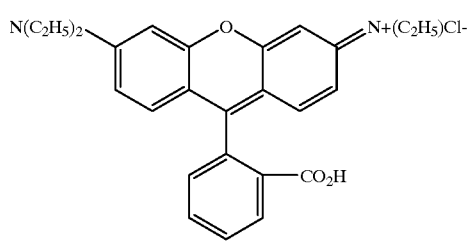

D&C Red #19 (XXXXIII; Rhodamine B)

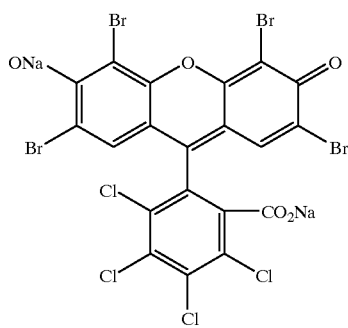

D&C Red #28 (XXXXIV)

e) the following anthroquinone derivatives:
   carmine (XIV)
   carminic acid (XV)

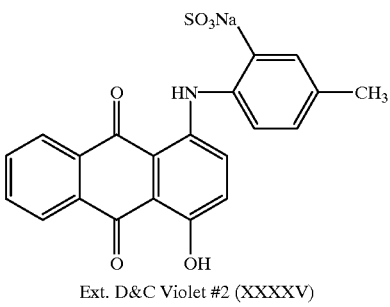

Ext. D&C Violet #2 (XXXXV)

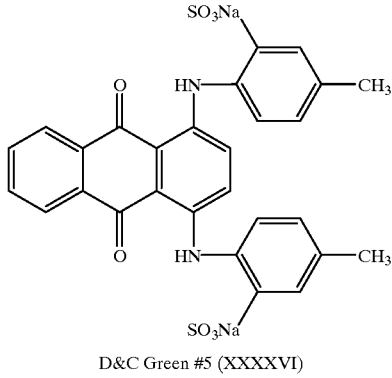

D&C Green #5 (XXXXVI)

f) the pyrene derivative D&C Green No. 8 (XVI); and
g) the following quinoline derivatives:

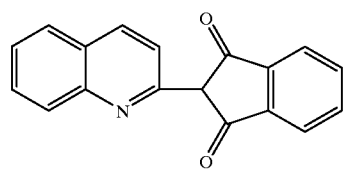

D&C Yellow #11 (XXXXVII)

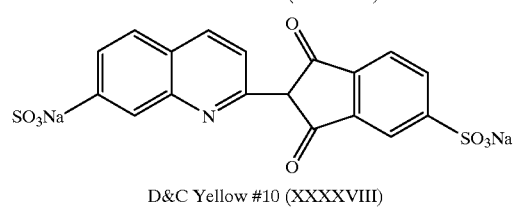

D&C Yellow #10 (XXXXVIII)

Each synthetic colorant was tested for activity as an inhibitor of EBV-EA induction in Raji cells according to the previously described method, and the results are recorded in Tables 3 and 4. In each of these tables, the entries have been arranged roughly in order of inhibitory activity toward EBV-EA induction, with the most active colorants being entered first. The tested synthetic colorants have been classified as:
   strongly effectively EBV-EA induction inhibitors if all EBV-EA induction is inhibited at a mole ratio of colorant to tumor promoter of 1000 or less;
   moderately effective EBV-EA induction inhibitors if the number of Raji cells exhibiting signs of EBV-EA induction in the presence of the colorant (mole ratio of colorant to tumor promoter=1000) is greater than 0% and less than 40% of the number of Raji cells exhibiting signs of EBV-EA induction in the absence of the colorant; and
   weakly effective or ineffective EBV-EA induction inhibitors if the number of Raji cells exhibiting signs of EBV-EA induction in the presence of the colorant (mole ratio of colorant to tumor promotor=1000) is greater than 40% of the number of Raji cells exhibiting signs of EBV-EA induction in the absence of the colorant.

The phenylazonapthalene derivative D&C Red #33 was found to be the most active among the colorant samples tested in vitro which are included in Table 3, followed by the azo compounds FD&C Yellow #5 and D&C Red #7. In fact, it appears that five of the ten most effective colorants included in Table 3 have azo groups. The results in Table 4, like those in Table 3, indicate that an azo compound is the most active of the colorants included. All of the azo compounds, with the exception of phenazopyridine hydrochloride, appear to show at least moderate anti-tumor promoting activity. While it is interesting to note that phenazopyridine hydrochloride is the only tested azo compound which has no acidic or anionic groups, it is unclear whether this is the cause of its low anti-tumor promoting activity, or merely an interesting coincidence. This would seem to indicate that azo compounds may have therapeutic utility as anti-tumor promoting agents.

TABLE 3

Inhibitory Effect of Synthetic Colorants on TPA-Induced EBV-EA Induction

| Colorant | % relative to control (% viability)* Colorant Concentration (mol ratio/TPA) | | | |
|---|---|---|---|---|
| | 1000 | 500 | 100 | 10 |
| D&C Red #33 | 0 (70) | 15.5 | 42.1 | 88.1 |
| FD&C Yellow #5 | 0 (70) | 37.1 | 65.8 | 89.0 |
| D&C Red #7 | 0 (70) | 44.7 | 65.0 | 89.5 |
| D&C Green #5 | 0 (70) | 0 | 66.5 | 93.7 |
| Olsal | 0 (60) | 11.2 | 65.9 | 100 |
| FD&C Yellow #6 | 0 (70) | 64.8 | 72.0 | 100 |
| Sulfasal | 0 (60) | 26.9 | 72.0 | 100 |
| Carminic Acid | 0 (70) | 65.8 | 88.0 | 100 |
| D&C Orange #4 | 0 (70) | 18.6 | 68.3 | 100 |
| D&C Red #22 | 0 (60) | 32.5 | 73.9 | 100 |
| Ext. D&C Violet #2 | 0 (70) | 0 | 87.0 | 100 |
| Carmine | 0 (70) | 26.4 | 91.5 | 100 |
| FD&C Blue #2 | 0 (70) | 43.7 | 91.4 | 100 |
| FD&C Red #40 | 19.6 (70) | 34.8 | 75.5 | 100 |
| D&C Orange #5 | 24.7 (70) | 57.2 | 82.6 | 100 |
| D&C Yellow #7 | 33.8 (60) | 54.0 | 76.3 | 100 |
| D&C Green #8 | 15.8 (60) | 39.3 | 84.0 | 100 |
| FD&C Green #3 | 17.9 (70) | 66.2 | 82.9 | 100 |
| D&C Yellow #8 | 16.7 (60) | 52.8 | 91.6 | 100 |
| FD&C Blue #1 | 12.8 (70) | 66.0 | 93.5 | 100 |
| D&C Yellow #10 | 16.3 (60) | 57.0 | 100 | 100 |
| D&C Red #6 | 32.3 (70) | 55.0 | 81.4 | 100 |
| D&C Orange #10 | 17.9 (70) | 81.3 | 100 | 100 |
| D&C Blue #6 | 25.1 (70) | 84.9 | 100 | 100 |
| Tetrachloro-fluorescein | 41.3 (60) | 63.9 | 82.0 | 100 |
| D&C Red #19 | 43.8 (60) | 69.2 | 85.9 | 100 |
| D&C Yellow #8 | 46.2 (60) | 67.3 | 86.9 | 100 |
| Phenazo | 47.2 (60) | 74.6 | 93.1 | 100 |
| D&C Red #21 | 45.1 (70) | 72.6 | 92.4 | 100 |
| D&C Red #28 | 53.8 (60) | 77.4 | 100 | 100 |
| FD&C Red #3 | 63.5 (70) | 85.7 | 100 | 100 |
| D&C Yellow #11 | 81.5 (70) | 100 | 100 | 100 |
| D&C Red #27 | 88.8 (70) | 100 | 100 | 100 |

*Values represent percentages of Raji cells showing EBV-EA induction (error ≦ ± 3%), measured relative to the positive control value (TPA 32 pmol = 100%). Values in parentheses are viability percentages of Raji cells.

TABLE 4

Inhibitory Effect of Synthetic Colorants on TPA induced EBV-EA Induction

| Colorant | % relative to control (% viability)* Colorant Concentration (micrograms/ml) | | | |
|---|---|---|---|---|
| | 10 | 1 | 0.1 | 0.01 |
| D&C Red #39 | 0 (69) | 61.7 | 88.2 | 100 |
| FD&C Red #3 | 32.4 (70) | 64.9 | 92.0 | 100 |
| FD&C Blue #1 | 32.6 (70) | 67.7 | 90.3 | 100 |
| FD&C Red #4 | 25.6 (60) | 87.2 | 100 | — |
| D&C Red 30, AI Lake | 21.4 (70) | 90.5 | 100 | 100 |

*Values represent percentages of Raji cells showing EBV-EA induction, measured relative to the positive control value (TPA 32 pmol = 100%). Values in parentheses are viability percentages of Raji cells.

The fluorescein colorants showed no clear pattern in their activity, with D&C Red # 22 (the disodium salt of tetrabromofluorescein) showing strong anti-tumor promoting activity, while D&C Yellow # 8, D&C Orange # 5 (dibromofluorescein), D&C Yellow # 7 (fluorescein), and D&C Orange # 10 (diiodofluorescein) exhibit moderate anti-tumor promoting activity. Tetrachlorofluorescein, D&D Red # 19 (Rhodamine B), D&C Red #27 (tetrachlorotetrabromofluorescein), D&C Red #28 (the disodium salt of D&C Red # 27), and FD&C Red #3 (the disodium salt of tetraiodofluorescein) were among the least active of the compounds studies.

As for the remaining compounds, the anthroquinone derivatives (carmine, carminic acid, D&C Green No. 5, and Ext. Violet No. 2) showed strong inhibitory activity toward EBV-EA induction. The quinoline derivatives D&C Yellow # 11 was an extremely inactive inhibitor of EBV-EA induction. Surprisingly, however, D&C Yellow #10 (as sulfonated derivative of D&C Yellow # 10), while not a strong EBV-EA inhibitor, did show significant anti-tumor promoting activity. The pyrene derivative (D&C Green No. 8) and the triphenylmethyl derivatives (FD&C Blue No. 1 and FD&C Green No. 3) were moderately active inhibitors of EBV-EA induction. The indigo-type compound of FD&C Blue No. 2 was a strongly effective anti-tumor promoting agent; however, other indigo-type compounds, D&C Blue No. 6 and the alum lake of D&C Red No. 30, were only moderately effective at best. The synthetic colorants studied all exhibited low cytotoxicity.

The vegetable extracts listed in Table 1 were also tested for in vitro inhibition of Epstein-Barr virus early antigen induction by TPA, and the results are recorded in Table 5.

TABLE 5

Inhibitory Effect of Vegetable Dye Extracts on TPA-Induced EBV-EA Induction

| Extract | % relative to control (% viability)* Extract Concentration (micrograms/ml) | | | |
|---|---|---|---|---|
| | 500 | 100 | 10 | 1 |
| Beet Root | 0 (60) | 8.3 | 40 | 89.4 |
| Grape** | — | 0 (70) | 57.2 | 85.7 |
| Capsanthin | 0 (70) | 19.5 | 54.3 | 87.5 |
| Cranberry | — | 45.1 | 90 | 100 |
| Red Onion Skin | — | 0 (60) | 65.6 | 87.2 |
| Long Red Bell Pepper | — | 54.0 (70) | 100 | 100 |
| Short Red Bell Pepper | — | 0 (70) | 25.0 | 80.4 |
| Purple Bell Pepper | — | 0 (70) | 18.5 | 85.7 |
| Green Bell Pepper | — | 0 (70) | 63.9 | 100 |
| Light Yellow Green Pepper | — | 0 (70) | 79.2 | 100 |

*Values represent percentages of Raji cells showing EBV-EA induction, measured relative to the positive control value (TPA 32 pmol = 100%). Values in parentheses are viability percentages of Raji cells.

TABLE 5-continued

Inhibitory Effect of Vegetable Dye Extracts on TPA-Induced EBV-EA Induction

| | % relative to control (% viability)* Extract Concentration (micrograms/ml) | | | |
|---|---|---|---|---|
| Extract | 500 | 100 | 10 | 1 |

**At 0.1 micrograms/ml extract concentration, the percentage of Raji cells showing EBV-EA induction, measured relative to the positive control value is 100%.

It is found that the beetroot extract, containing high levels of betanin, inhibits EBV-EA induction by TPA quite strongly. In fact, beetroot extract is more effective at EBV-EA inhibition than capsinthin, a colorant found in paprika. Grape extract was also found to be an effective inhibitor of EBV-EA induction, exhibiting an activity which appears to be greater than that of capsinthin, although not as great as that of beet root extract. Red onion skin extract, although possessing some inhibitory activity toward TPA-induced EBV-EA induction, was found to be less active than beetroot extract, grape extract, or capsanthin, Cranberry and long red bell pepper inhibited EBV-EA induction less strongly than red onion skin extract. Interestingly, long red bell pepper was the least active of the six extracts studied, while short red and purple bell peppers were the most active, exhibiting slightly greater activity than beetroot extract. The activity of the green and light yellow green bell peppers were roughly as active as red onion skin. It is unclear why the different types of bell pepper extracts have such widely varying activity. None of the vegetable extracts studied showed unacceptable levels of cytotoxicity.

From the above data, it would appear that the beetroot extract, containing betanins as the primary colorants, is an effective inhibitor of EBV-EA induction. More particularly, it seems that betanins are more effective inhibitors of EBV-EA induction than capsinthin, one of the primary carotenoid colorants in paprika, or the anthocyanins, the primary colorants in cranberry and red onion skin. The data presented does not allow us to make a clear comparison between the inhibitory activity of betanins and the carotenoids, the primary colorants in both long and short red bell peppers. Nevertheless, the results do not seem to indicate that beetroot extracts containing betanins possess potential as inhibitors of TPA-induced tumor formation.

With regard to the vegetable extracts discussed above, it must be noted that it is unproven that the anti-tumor promoting activity is due to colorant compounds. Since the extracts were crude, the anti-tumor promoting activity may be due to a non-colorant compound present in an extract.

The thirty-seven colorant formulations derived from paprika, turmeric, and/or annatto seeds listed in Table 2 were also tested for in vitro inhibition of Epstein-Barr virus early antigen induction by TPA. The results of these tests are recorded in Table 6.

TABLE 6

Inhibitory Effect of Colorants Derived from Paprika, Turmeric, and/or Annatto Seeds on TPA-Induced EBV-EA Induction

| Colorant Formulation | % relative to control (% viability)* Colorant Concentration (micrograms/ml) | | | Cytotoxic? |
|---|---|---|---|---|
| | 100 | 10 | 1 | |
| 1 | 0 (20) | 0 (60) | 67.2 | yes |
| 2 | 0 (10) | 46.1 (70) | 89.4 | yes |
| 3 | 16.4 (0) | 42.7 (60) | 69.5 | yes |
| 4 | 0 (79) | 48.3 | 67.2 | no |
| 5 | 28.7 (0) | 100 (60) | 100 | yes |
| 6 | 36.7 (20) | 85.3 (70) | 100 | yes |
| 7 | 0 (70) | 80.1 | 100 | no |
| 8 | 90.6 (70) | 100 | 100 | no |
| 9 | 0 (70) | 44.7 | 100 | no |
| 10 | 72.8 (70) | 93.8 | 100 | no |
| 11 | 0 (0) | 45.9 (60) | 93.2 | yes |
| 12 | 0 (0) | 64.7 (60) | 95.5 | yes |
| 13 | 33.9 (60) | 58.0 | 100 | no |
| 14 | 17.4 (60) | 100 | 100 | no |
| 15 | 0 (60) | 36.8 | 90.2 | no |
| 16 | 0 (60) | 57.4 | 92.5 | no |
| 17 | 30.7 (70) | 84.0 | 100 | no |
| 18 | 10.6 (0) | 46.9 (70) | 86.1 | yes |
| 19 | 0 (0) | 45.4 (70) | 73.0 | yes |
| 20 | 0 (0) | 58.9 (60) | 80.4 | yes |
| 21 | 0 (60) | 27.3 | 77.9 | no |
| 22 | 0 (0) | 35.5 (60) | 73.0 | yes |
| 23 | 15.7 (0) | 59.4 (60) | 93.7 | yes |
| 24 | 0 (0) | 46.3 (60) | 89.6 | yes |
| 25 | 18.6 (80) | 100 | 100 | no |
| 26 | 25.9 (70) | 90.6 | 100 | no |
| 27 | 0 (20) | 82.7 (70) | 100 | yes |
| 28 | 28.4 (30) | 67.6 (70) | 100 | yes |
| 29 | 0 (50) | 93.0 | 100 | yes |
| 30 | 0 (50) | 75.4 | 100 | yes |
| 31 | 0 (80) | 63.8 | 100 | no |
| 32 | 0 (70) | 64.6 | 100 | no |
| 33 | 32.6 (80) | 66.3 | 84.9 | no |
| 34 | 45.2 (80) | 73.7 | 92.8 | no |
| 35 | 0 (80) | 20.4 | 85.6 | no |
| 36 | 0 (50) | 66.9 (70) | 100 | yes |
| 37 | 19.5 unknown | 54.3 | 87.5 | |

*Values represent percentages of Raji cells showing EBV-EA induction, measured relative to the positive control value (TPA 32 pmol = 100%). Values in parentheses are viability percentages of Raji cells.

Based on the data in Table 6, the colorant formulations have been classified as:

a) strongly effectively EBV-EA induction inhibitors if:
  i) all EBV-EA induction is inhibited at a colorant concentration of 100 micrograms/ml or less; and
  ii) the number of Raji cells exhibiting signs of EBV-EA induction in the presence of the colorant formulation (colorant concentration=10 micrograms/ml) is less than 60% of the number of Raji cells exhibiting signs of EBV-EA induction in the absence of the colorant.

b) moderately effective EBV-EA induction inhibitors if:
  i) the number of Raji cells exhibiting signs of EBV-EA induction in the presence of the colorant formulation (colorant concentration=100 micrograms/ml) is greater than 0% and less than 50% of the number of Raji cells exhibiting signs of EBV-EA induction in the absence of the colorant; or
  ii) all EBV-EA induction is inhibited at a colorant concentration of 100 micrograms/ml; and the number of Raji cells exhibiting signs of EBV-EA induction in the presence of the colorant formulation at a colorant concentration of 10 micrograms/ml is greater than 60% of the number of Raji cells exhibiting signs of EBV-EA induction in the absence of the colorant; and c) weakly effective or ineffective EBV-EA induction inhibitors if the number of Raji cells exhibiting signs of EBV-EA induction in the presence of the colorant formulation at a colorant concentration of 100 micrograms/ml is greater than 50% of the number of Raji cells exhibiting signs of EBV-EA induction in the absence of the colorant. By applying this system to the results presented in Table 6, the colorant formulations listed in Table 2 have been classified as follows:

strongly active: 1, 2, 4, 9, 11, 15, 16, 19, 20, 21, 22, 24, and 35 moderately active: 3, 5, 6, 7, 12, 13, 14, 17, 18, 23, 25, 26, 27, 28, 29, 30, 31, 32, 33, 34, 36, and 37 weakly active or inactive: 8 and 10

From the data in table 6, it appears that colorant formulation No. 1, a turmeric extract containing 85–97% curcumin which inhibits all EBV-EA induction at a colorant concentration of 10 micrograms/ml, is the most effective of these compositions as an inhibitor of EBV-EA induction. However, when cell toxicity studies were conducted, it was found that at high concentration of the colorant (100 micrograms/ml), only 20% of the Raji cells used in the EBV-EA activation assay survived exposure to colorant formulation No. 1. In fact, over 45% of the tested compositions derived from paprika, turmeric, and/or annatto seeds showed unacceptably high levels of cytotoxicity (see Table 6). Even if these cytotoxic compositions possess sufficient inhibitory activity toward EBV-EA induction to suggest that they have utility as anti-tumor promoting or cancer chemopreventive agents, the high levels of cytotoxicity raise human health concerns that would argue against their therapeutic use.

Fortunately, several of the compositions derived from paprika, turmeric, and/or annatto seeds showed acceptably low levels of cytotoxicity toward Raji cells in the EBV-EA activation test. At least 60% of the Raji cells exposed to these colorant formulations of a colorant concentration of 100 micrograms/ml survived. Based on the data in Table 6, the non-cytotoxic colorant formulations have been classified in the following manner with regard to their inhibitory activity toward TPA-induced EBV-EA induction.

strongly active: 4, 9, 15, 16, 21, and 35 moderately active: 7, 13, 14, 17, 25, 26, 31, 32, 33, and 34 weakly active or inactive: 8 and 10

Out of the six most effective non-cytotoxic compositions showing anti-tumor activity, two (No. 4 and No. 35) are composed of natural extractives of annatto seeds and turmeric in a vehicle made from polysorbate 80, KOH, and propylene glycol. The activity of this formulation against EBV-EA induction was greater than that of the annatto seed-derived pigment bixin itself (colorant formulation No. 36) but somewhat less than that of turmeric containing 85–97% curcumin (colorant formulation No. 1). Formulations No. 4 and No. 35 also show much lower cytotoxicity than formulations No. 1 and No. 36, suggesting that therapeutic use of a blend of natural extractives of annatto seeds and turmeric as anti-tumor promoting or cancer chemopreventive agents may pose lower health risks than use of purified pigments from either turmeric or annatto seeds alone. Similarly, colorant formulation No. 21, composed of natural extractives of paprika with vegetable oil showed higher inhibitory activity toward EBV-EA induction than that of the pure paprika-derived pigment capsanthin in vegetable oil (colorant formulation No. 37), coupled with low cytotoxicity. Colorant formulation No. 15, composed of natural extractives of annatto seeds with propylene glycol, water, and KOH, appears to show greater anti-tumor promoting activity and slightly lower cytotoxicity than colorant formulation No. 36, containing the pigment bixin. Interestingly, the activity against EBV-EA induction shown by some natural extractives from paprika and annatto seeds appears to be greater than that of the purified pigments from paprika and annatto seeds.

Other colorant formulations that appear from this data to be particularly effective inhibitors of EBV-EA induction include:

natural extractives of annatto seeds and turmeric in a medium comprising vegetable oil and fumed silicon dioxide; and extractives of annatto seeds having a norbixin content of 2.6–4.0 wt. % in a medium comprising water and KOH.

2. In Vivo Studies on Inhibition of Carcinogenesis in Mice 2.1 Materials and Methods Two-stage mouse skin carcinogenesis tests were conducted on mice. Each group of mice was composed of 15 mice housed 5 per cage. Basal diet and tap water were available ad libitum throughout the experiment following the method of Tokuda et al. (Tokuda et al., *Oncology*, 48, 77–80 [1991]).

Studies on inhibition of TPA-induced skin carcinogenesis by synthetic colorants were conducted on 6-week-old female mice, specific pathogen-free ICR strain, using the following procedure. The back of each mouse was shaved with surgical clippers. Each mouse was then treated topically with 390 nmol 7,12-dimethylbenz[a]anthracene (DMBA) in 0.1 ml acetone. One week before TPA-treatment, each mouse in a test group was treated with an acetone solution of the test dye (85 nM). A control group was not treated with dye. The incidence of papillomas was observed weekly for twenty weeks.

Studies on inhibition of DMBA-TPA induced skin carcinogenesis by plant extracts and plant pigments were conducted on 6-week-old female mice, specific pathogen-free ICR strain, using the following procedure. The back of each mouse was shaved with surgical clippers. Each mouse was then treated topically with 390 nmol 7,12-dimethylbenz[a]anthracene (DMBA) in 0.1 ml acetone. After 1 week, each mouse received topically 1.7 nmol TPA in 0.1 ml acetone twice weekly for twenty weeks. During TPA treatment, a test group of mice was given drinking water containing a defined test compound, while a control group was given water containing no test compound. For betanin studies a 0.0025% solution of beetroot extract was given orally to the mice (2.5 mg/100 ml $H_2O$). In studies of paprika and annatto seed extract formulations, the formulations were dissolved in a small volume of ethanol and diluted by water (2.5 mg extract/100 ml $H_2O$ to provide a 0.0025% solution). The incidence of papillomas was observed weekly for twenty weeks.

Studies of inhibition of NOR1-TPA induced skin carcinogenesis by betanins were conducted on 6-week-old female mice, specifically pathogen-free ICR strain, using the following procedure. The back of each mouse was shaved with surgical clippers. One week prior to initiation, each mouse in a test group was provided with drinking water containing 0.0025 wt % betanins. A control group was provided with drinking water containing no betanins. Each mouse was then treated topically with 390 nmol of NOR1 in 0.1 ml acetone for a week. One week after initiation, oral feeding of betanins to the test group was replaced with oral feeding of pure water. All animals in each group were treated topically with 1.7 nmol TPA in 0.1 ml acetone twice for twenty weeks. The incidence of papillomas on each mouse was observed weekly for twenty weeks.

A similar test was performed for inhibition of ultraviolet radiation-induced skin carcinogenesis. The mice used were 6-week-old female hairless mice, specific pathogen-free Hos;HR-1 strain. Each mouse was treated topically with 390 nmol 7,12-dimethylbenz[a]anthracene (DMBA) in 0.1 ml acetone for a week. After 1 week, each mouse was exposed to UVB radiation for eight minutes twice a week for twenty weeks. The ultraviolet radiation was applied at a dosage of 3,430 J/m$^2$. During TPA treatment, a test group of mice were given drinking water containing 0.0025% beetroot extract (2.5 mg extract/100 ml of water), while a control group was given water containing no beetroot extract. The incidence of papillomas was observed weekly for twenty weeks. The lamps used for irradiation of the test mice were Toshiba FL20 S.E. lamps, emitting UV radiation in the 280–320 nm range, with a peak at 305 nm.

Bioassays for inhibition of glycerol-promoted pulmonary tumor formation in mice were also performed. The animals used were ICR male mice. In each group of 15 mice, 0.3 mg of 4-nitroquinoline 1-oxide (4NQO) was injected into the back of each mouse as an initiator. After 5 weeks, a first group of mice was maintained with an 8% glycerol solution as its only source of drinking water. A second group was maintained with 0.0025% betanin solution (2.5 mg/100 ml of 8% glycerol). A third, control group was maintained with water alone. Two additional groups which were not subjected to treatment with 4NQO were also tested. One of these non-4NQO-treated groups was maintained with water alone; the other was maintained with 8% glycerol. After 25 weeks, all mice were sacrificed by cervical dislocation and autopsy was performed. Lung tumors (adenoma) were counted after separation of each pulmonary lobe. Statistical analysis was done using Student's t-test.

Bioassays for inhibition of liver carcinogenesis tumor formation in mice were also performed. The animals used were ICR female mice. In each of several groups of 15 mice, each mouse was treated with a single dose of 30 mg/kg body weight of N-nitrosodiethylamine as an initiator. After 1 week, each animal in a first control group and a test group of mice was treated with 0.09% phenobarbitol to promote carcinogenesis. The control group was maintained with an 0.09% phenobarbitol solution as its only source of drinking water. The test group was maintained with an 0.09% phenobarbitol solution containing 0.0025% betanins (2.5 mg/100 ml) as its drinking water. A second control group of mice was treated with a single dose of 30 mg/kg body weight of N-nitrosodiethylamine as an initiator, and maintained on pure drinking water with no betanins. This group was not treated with phenobarbitol. A third control group was not treated with DEN, and was maintained with an 0.09% phenobarbitol solution as its only source of drinking water. A fourth control group was not treated with DEN or phenobarbitol, and was maintained with pure water as its only source of drinking water. After 20 weeks, all mice were sacrificed by cervical dislocation and their livers were excised. Hyperplastic nodules were then counted and recorded. Statistical analysis was done using Student's t-test.

The standard mouse ear edema method was followed for the evaluation of anti-inflammatory activity. Indomethacin was used as a control. Seven-week-old ICR male mice were used for the test. On the left side of a mouse's ear, 10 micrograms TPA in 10 microliters acetone were applied. On the right side of the mouse's ear, 10 micrograms TPA and a defined amount of a test compound in 10 microliters acetone were applied. After a defined period of time, a portion of TPA-treated mouse ear was removed and weighed. At the same time, a portion of TPA and test compound-treated mouse ear of the same size and shape as the portion of TPA-treated mouse ear was removed and weighed. Any increase in weight over a section of non-treated mouse ear was taken as a measure of inflammation.

Six-week-old ICR mice and 7-week-old ICR mice were purchased from Japan SLC, Inc., Shizuoka, Japan. Six-week-old Hos:HR-1 mice were purchased from Hoshino Animal Factory, Saitama, Japan. Acetone, DMBA, glycerol, 4NQO, and TPA were purchased from Wako Pure Chemical Industries, Osaka, Japan.

2.2 Results and Discussion

Two of the synthetic colorants tested for in vitro inhibition of TPA-induced EBV-EA induction were also studied in vivo to determine whether they inhibited TPA-induced tumor formation in mice. The studies were conducted using a two-stage mouse skin carcinogenesis bioassay. The colorants studies were tartrazine (FD&C Yellow # 5), which was among the most active colorants tested in the in vitro EBV-EA induction assay, and erythosine B (FD&C Red #3), which was one of the least active colorants.

Figure 2:
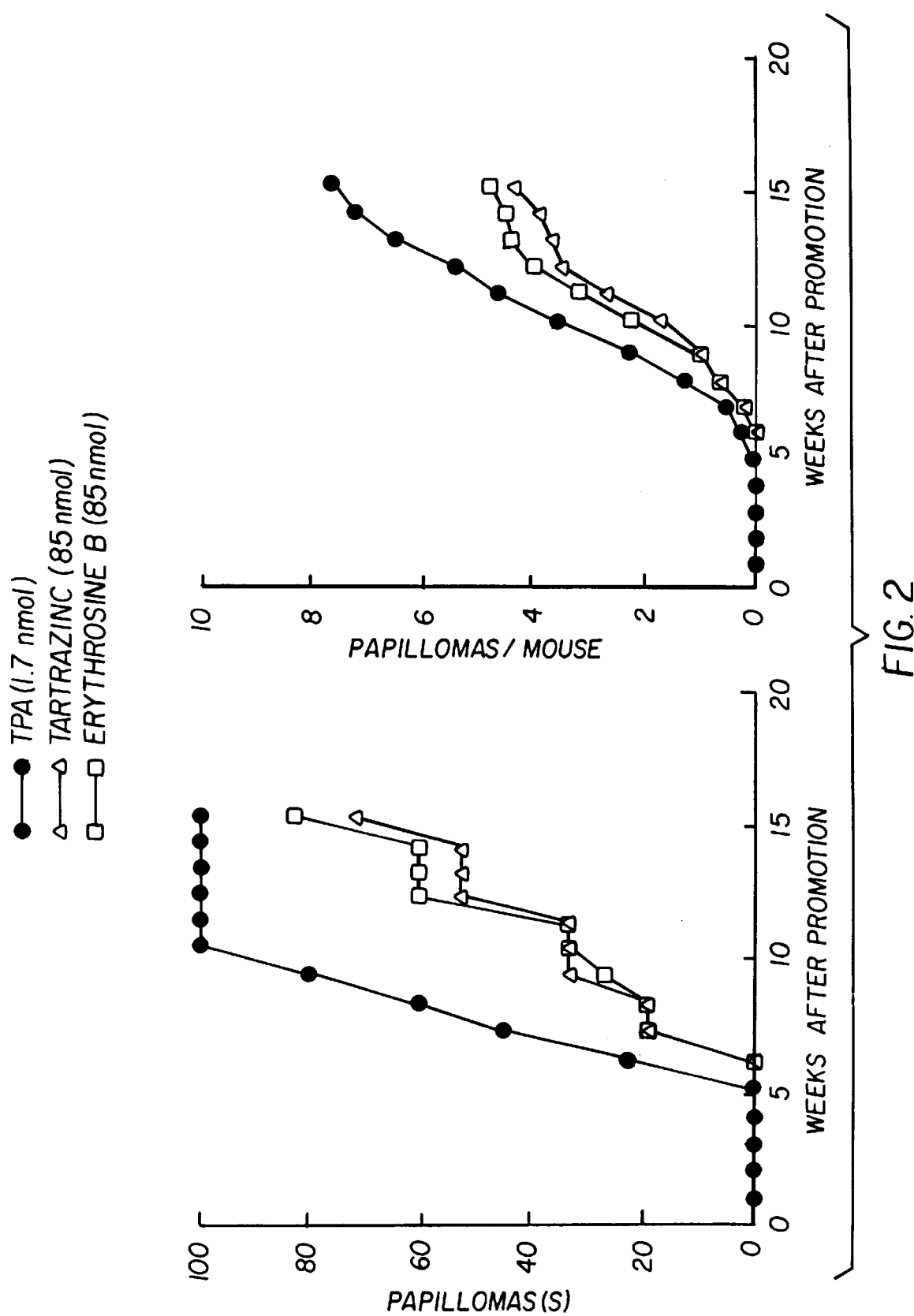
FIG. 2 shows the inhibitory effect of the synthetic colorants tartrazine and erythrosine B on TPA-promoted mouse skin tumor promotion.

The results are presented in FIG. 2. FIG. 2 shows the percentage of papillomas (or, more precisely, the percentage of mice having papillomas) formed with and without colorant treatment over a period of twenty weeks. The control animals, without the colorant treatment, show 100% incidence of papillomas in less than ten weeks. The test animals, which have been treated with colorant, take 15 weeks to show even 80% papilloma formation. This is also seen in the number of papillomas formed per mouse over a fifteen week period (FIG. 2). As seen, both the colorants appear to cause a 40% reduction in the number of papillomas per mouse. Thus, tartrazine and erythrosine B both show inhibitory activity toward TPA-induced two stage skin carcinogenesis.

Figure 3:
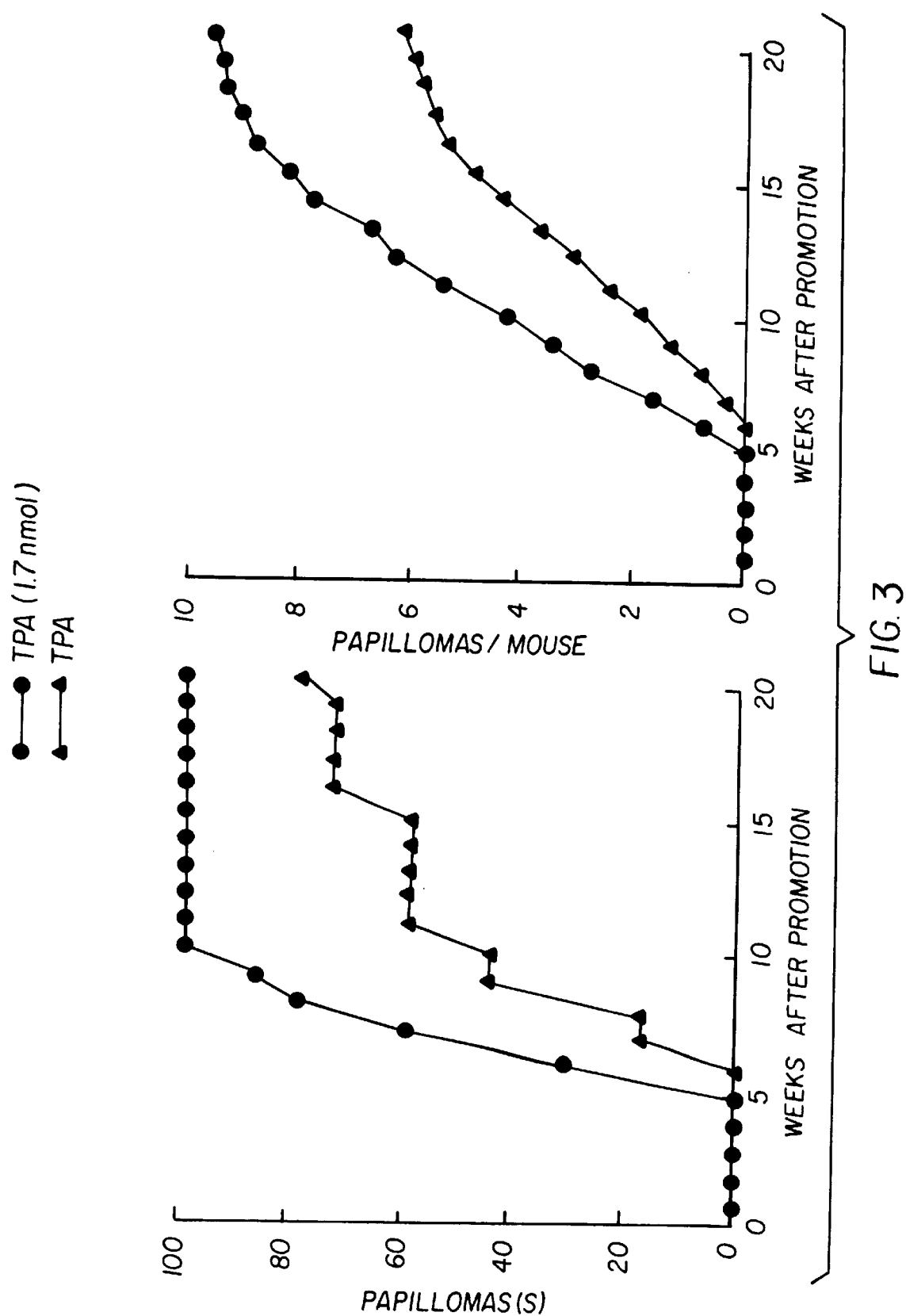
FIG. 3 shows the inhibitory effect of beetroot extract (betanin) on TPA-promoted mouse skin tumor promotion.
Figure 4:
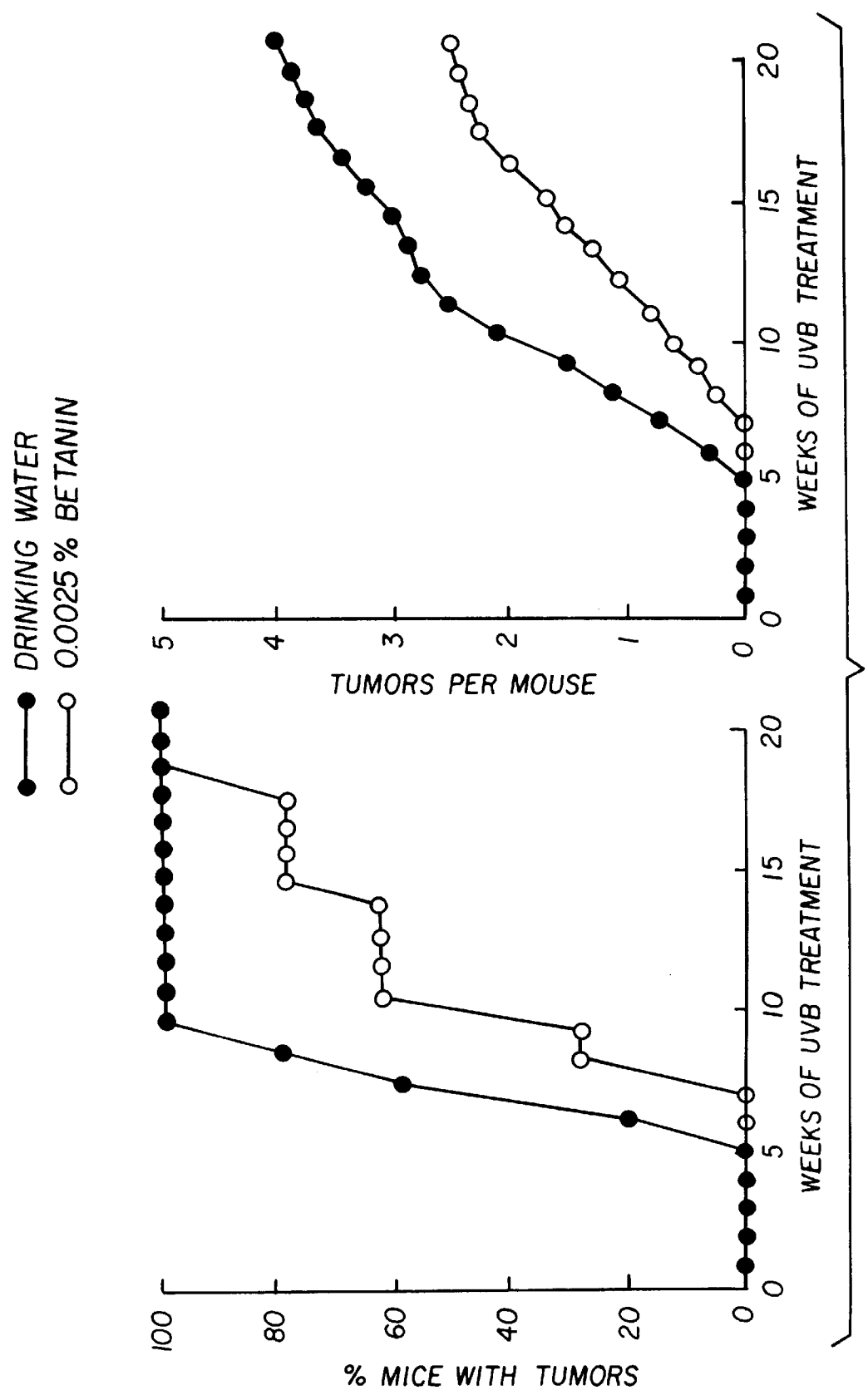
FIG. 4 shows the inhibitory effect of beetroot extract (betanin) on ultraviolet B radiation-promoted mouse skin tumor promotion.

Beetroot extract (betanin) was also tested for inhibitory activity toward TPA-induced tumor formation in mice using a two-stage mouse skin carcinogenesis bioassay. As shown in FIGS. 3 and 4, oral ingestion of betanin in ICR mice inhibited TPA-induced promotion of mice skin tumors. Both the percentage of mice having papillomas and the number of papillomas formed per mouse are significantly lower in mice given a betanin solution to drink than they are in mice given substantially pure water. Either DMBA (FIG. 3) or NOR1 (FIG. 4) may be used as an initiator.

Figure 5:
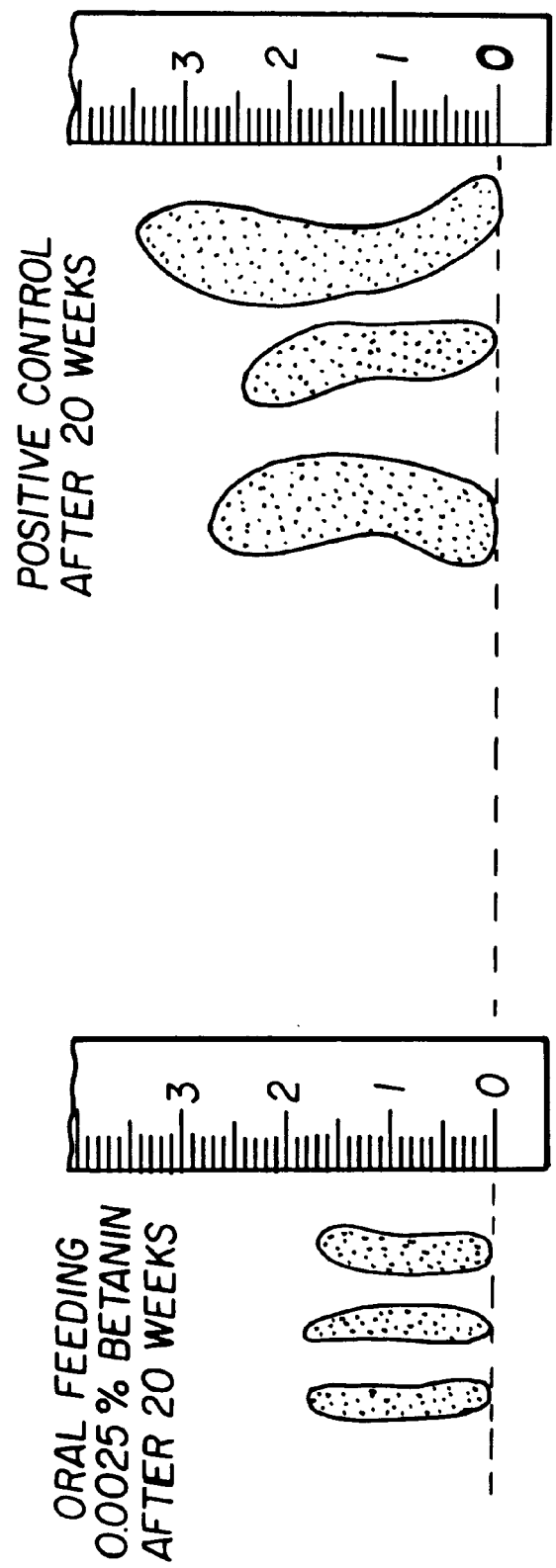
FIG. 5 shows the spleens of mice subjected to UV radiation treatment for twenty weeks. Those from mice maintained on water alone show pronounced enlargement (splenomegalia); those from mice maintained on water containing 0.0025% betanin do not.
Figure 6:
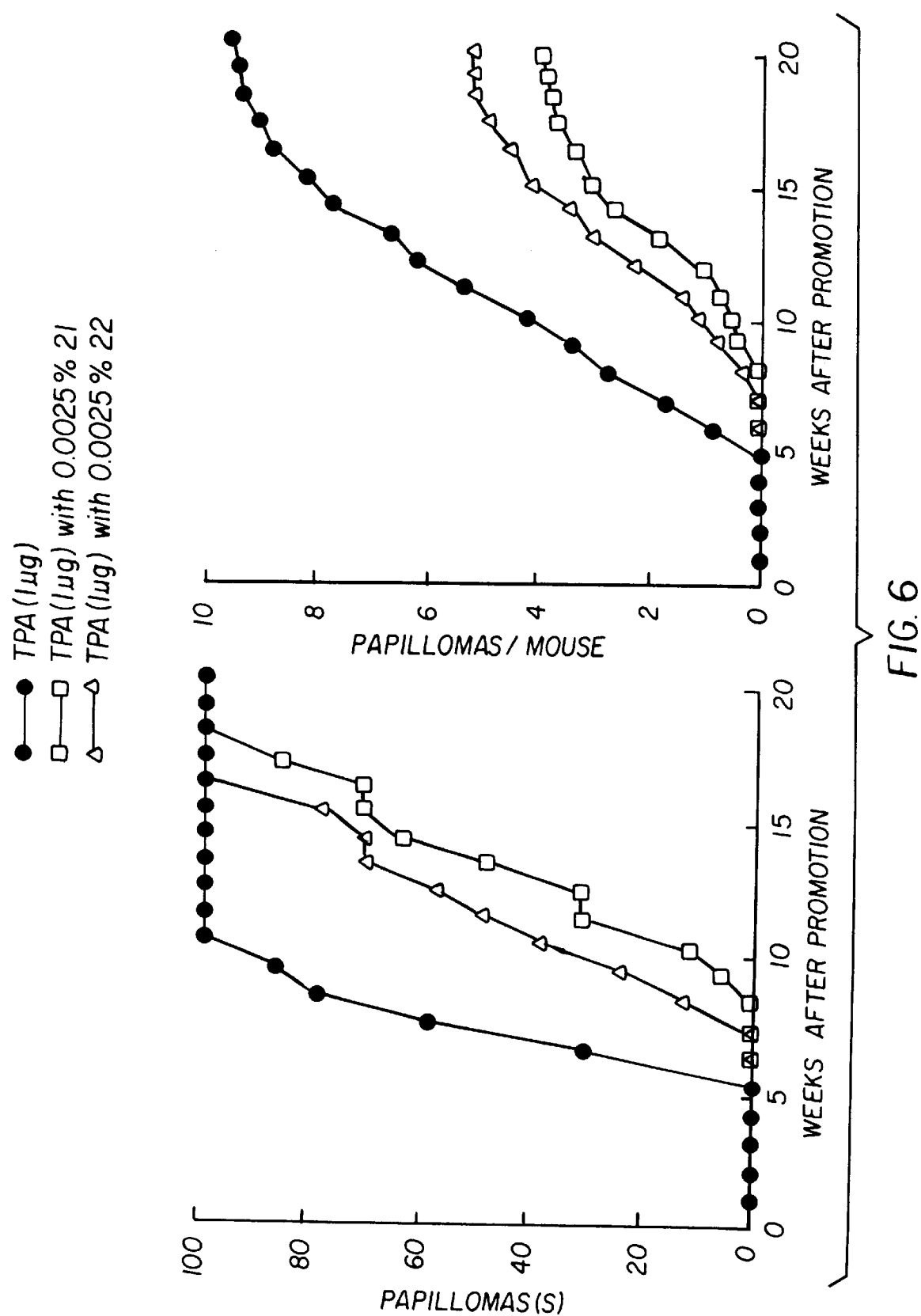
FIG. 6 shows the inhibitory effect of natural extracts of annatto seeds and paprika on TPA-promoted mouse skin tumor promotion.

Oral ingestion of betanin in Hos:HR-1 mice also acts to inhibit UVB radiation-promoted skin carcinogenesis, as shown in FIG. 5. The control animals, drinking water alone, show 100% incidence of papillomas in less than ten weeks of radiation treatment. In the same period, only 25% of the test animals, drinking water containing 0.0025% betanin, show any incidence of tumors. The test animals take 15 weeks to show even 80% papilloma formation. Evidence of anti-tumor activity is also seen in the number of papillomas formed per mouse over a twenty-week period. Oral feeding of betanin in drinking water causes a 40% reduction in the number of tumors per mouse, compared to the number of tumors per mouse in a control group of mice maintained on water alone. The mice in the control group were also found to show splenomegalia ("hypertrophia spleen"). The test animals, which were fed betanin in drinking water, did not show splenomegalia. FIG. 6 provides a visual comparison of the spleens of mice subjected to UVB radiation treatment for twenty weeks while being maintained on water alone (positive control) and the spleens of mice subjected to radiation treatment while being maintained on water containing 0.0025% betanin. This would seem to indicate that betanin is an effective inhibitor of ultraviolet B irradiation-induced skin tumor formation, and also affords protection against UVB irradiation-induced splenomegalia.

Beetroot extract was also tested for inhibitory activity toward pulmonary tumor formation. As shown in Table 7, oral ingestion of beetroot extract in drinking water containing 8% glycerol leads to a 60% reduction of lung tumors in 4NQO-treated mice, compared to 4NQO-treated mice maintained an 8% solution of glycerol alone. These findings, together with the findings of skin tumor formation indicate that beetroot is a useful cancer preventive vegetable.

TABLE 7

Incidence of Pulmonary Tumors in Mice Treated with Betanins

| Group Treatment | Body Wt. (g) | 8% Glyceorl Intake (ml/day/mouse) | Total No. of Tumors | No. of Tumors per mouse | % of Mice with Tumors |
| --- | --- | --- | --- | --- | --- |
| I Water alone | 47.6 ± 4.8 | 8.0 | 0 | 0 | 0 |
| II 8% glycerol | 56.4 ± 5.4 | 8.8 | 0 | 0 | 0 |
| Initiation + promotion | | | | | |
| III 4NQO + water | 46.6 ± 4.6 | 7.9 | 3 | 0.2 ± 0.1 | 6.6 |
| IV 4NQO + 8% glycerol | 55.2 ± 4.9 | 8.6 | 50 | 3.3 ± 0.5 | 100 |
| V 4NQO + 8% glycerol + 0.0025% betanins | 55.0 ± 5.1 | 8.6 | 14 | 0.9 ± 0.3 | 40 |

Notes:
a) Groups of 15 mice were effective numbers at the end of the experiment.
b) No statistically significant differences were observed between groups by mean intake of drinking.
c) The increase in the body weight of the treated mice was not affected by treatment with betanins.

TABLE 8

Anti-Inflammatory Activity of Paprika and Annatto Seed Extracts

| Concentration | Test Compounds | | |
| --- | --- | --- | --- |
| (1 μg/10 ml acetone) | Indomethacin | KaI-21 | KaI-22 |
| 100 | +++ | ++ | ++ |
| 10 | ++ | + | − |
| 1 | + | − | − |

KEY
+++ = strongest anti-inflammatory activity
++ = strong anti-inflammatory activity
+ = weak anti-inflammatory activity
− = no anti-inflammatory activity
*On left side of the mouse's ear, 10 μg TPA in 10 μl acetone were applied. On right side of the mouse's ear, 10 μg TPA in 10 μl acetone were applied, together with a defined amount of test compound in 10 μl acetone.

Two of the colorant formulations derived from turmeric, annatto seeds, and/or paprika were also tested for inhibition of TPA-induced tumor formation in mice, and the results are shown in FIG. 7. A control group of mice maintained on water alone showed 100% incidence of skin tumors in ten weeks. By comparison, a test group of mice maintained on water containing 0.0025% colorant formulation # 21, composed of natural extractives of paprika with vegetable oil, showed only 80% incidence of tumors after 15 weeks. A 60% reduction in the number of tumors per mouse was also observed at the end of a twenty-week period. Another test group of mice was maintained on water containing 0.0025% colorant formulation # 22, composed of natural extractives of annatto seeds with vegetable oil. Formulation # 22 was less effective than formulation # 21, showing 80% incidence of tumors after only 13 weeks. More tumors per mouse were seen after twenty weeks in mice fed formulation # 22 than in those fed formulation # 21. Additionally, the in vitro results presented in Table 6 indicate that formulation # 21 has significantly lower cytotoxicity than formulation # 22. This data would seen to indicate that a composition of natural extractives of paprika with vegetable oil may have potential therapeutic utility as an anti-tumor promoting or cancer chemopreventive agent.

Formulation # 21 and formulation # 22 were also tested for anti-inflammatory activity by the mouse ear edema method. Both formulations exhibited anti-inflammatory activity, with formulation # 21 showing greater activity than # 22. The results are provided in Table 8. As can be seen, the extractive of paprika in vegetable oil (formulation # 21) exhibited comparatively strong anti-inflammatory activity as compared to indomethacin. The extractive of annatto seeds with vegetable oil (formulation # 22) showed lower activity than # 21. It is possible that paprika extractives may be therapeutically useful anti-inflammatory agents.

Carcinogenesis of the liver is yet another formidable cancer that may have environmental origins. Use of dietary constituents as chemopreventive agents would be of immense value. We have, therefore, extended our studies of betanin as chemopreventive agents to hepatocarcinogenesis.

The results of the study of betanins as potential chemopreventive agents of liver carcinogenesis indicated that in the control group treated with DEN and 009% phenobarbitol a large number of hyperplastic nodules appeared, whereas in the group treated with DEN as initiator, phenobarbitol as a promoter, and 00025% batanin as inhibitor there was a reduction noticeable in the occurrence of nodules. Thus, it was clear that betanin treatment indeed reduced the number of hyperplastic nodules. Detailed analysis of this study is shown in Table 8. As stated above, treatment with 0.0025% betanin reduces the hyperplastic nodules in these animals by over 50%. The percentage of mice with hyperplastic nodules is also reduced to less than 50%. It should also be noted that the control animals treated with DEN or phenobarbitol alone did not develop any hyperplastic nodules.

What is claimed is:
1. A method of inhibiting Epstein-Barr virus early antigen induction in Epstein-Barr virus genome-carrying cells comprising the steps of:
   a) cultivating the Epstein-Barr virus genome-carrying cells in a medium containing at least one chemical selected from the group consisting of tumor-inducing chemicals and tumor-promoting chemicals; and b) adding an effective amount of a synthetic colorant to the medium, said effective amount being sufficient to inhibit Epstein-Barr virus early antigen induction in Epstein-Barr virus genome-carrying cells;

wherein the synthetic colorant is selected from the group consisting of a compound of formula VIII:

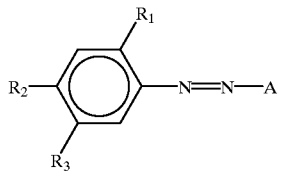
(VIII)

wherein A is selected from the group consisting of:

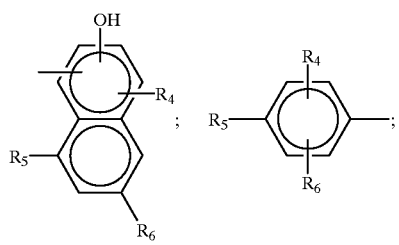

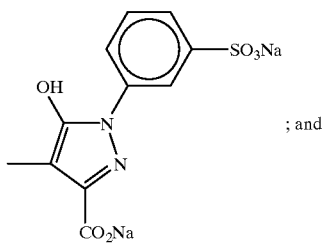
; and

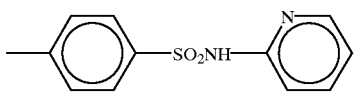

wherein R1 is —H, lower alkyl, lower alkoxy, —CO2M, —SO3M; R2 is —H, lower alkyl, or —SO3M; R3 is —H, lower alkyl, or —SO3M; R4 is —H, —CO2M, or —SO3M; and R5 and R6, which may be the same or different, are independently selected from the group consisting of —H, —OH, —NL2, CO2M, and —SO3M; L is —H, lower alkyl, or lower hydroxyalkyl; and M is —H, an alkali metal cation, or an alkaline earth metal cation; and wherein the steps of cultivating the Epstein-Barr virus genome-carrying cells in the medium and adding the colorant to the medium are each performed in vitro.

2. The method of claim 1, wherein A is

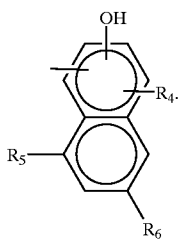

3. The method of claim 1, wherein A is

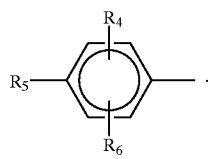

4. The method of claim 1, wherein A is

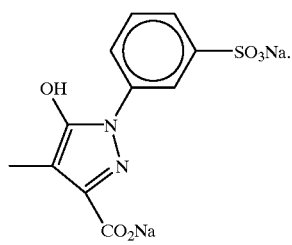

5. The method of claim 1, wherein A is

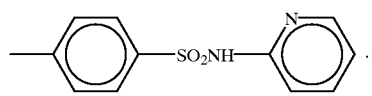

6. The method of claim 1, wherein a tumor-promoting chemical is present in the medium, said medium being an RPMI 1640 medium.

7. The method of claim 1, wherein a tumor-inducing chemical is present in the medium, said medium being an RPMI 1640 medium.

8. The method of claim 1, wherein a tumor-inducing chemical and a tumor-promoting chemical are present in the medium, said medium being an RPMI 1640 medium.

9. The method of claim 6, wherein the tumor-promoting chemical is 12-O-tetradecanoylphorbol-13-acetate.

10. The method of claim 7, wherein the tumor-inducing chemical is dimethyl[α]benzanthracene.

11. The method of claim 8, wherein the tumor-promoting chemical is 12-O-tetradecanoylphorbol-13-acetate and the tumor-inducing chemical is dimethyl[α]benzanthracene.

12. A method of inhibiting Epstein-Barr virus early antigen induction in Epstein-Barr virus genome-carrying cells comprising the steps of:

a) cultivating the Epstein-Barr virus genome-carrying cells in a medium containing at least one chemical selected from the group consisting of tumor-promoting chemicals and tumor-inducing chemicals; and b) treating the cells with a synthetic colorant, wherein the synthetic colorant is selected from the group consisting of FD&C Red #4, FD&C Red #40, FD&C Yellow # 6; D&C Orange # 4; D&C Red # 6; D&C Red # 7; D&C Red # 33; D&C Red # 39; FD&C Yellow # 5; olsalazine; sulfasalazine; and mixtures thereof;

wherein the steps of cultivating the Epstein-Barr virus genome-carrying cells in the medium and treating the cells with the synthetic colorant are each performed in vitro.

13. The method of claim 12, wherein the tumor-promoting chemical is 12-O-tetradecanoylphorbol-13-acetate.

14. The method of claim 12, wherein the tumor-initiating chemical is dimethyl[α]benzanthracene.

15. The method of claim 12, wherein the synthetic colorant is FD&C Yellow # 6.

16. The method of claim 12, wherein the synthetic colorant is D&C Orange # 4.

17. The method of claim 12, wherein the synthetic colorant is D&C Red # 7.

18. The method of claim 12, wherein the synthetic colorant is D&C Red # 33.

19. The method of claim 12, wherein the synthetic colorant is FD&C Yellow # 5.

20. The method of claim 12, wherein the synthetic colorant is olsalazine.

21. The method of claim 12, wherein the synthetic colorant is sulfasalazine.

22. The method of claim 12, wherein the cells have been cultivated by incubation at 37° C. in 1 ml of an RMPI 1640 medium containing the tumor promoter 12-O-tetradecanoylphorbol-13-acetate in a concentration of 32 pM and butyric acid in a concentration of 4 mM.

23. The method of claim 12, wherein the synthetic colorant is added to the cultivation medium in a concentration which is between 100 times the 12-O-tetradecanoylphorbol-13-acetate concentration and 1000 times the 12-O-tetradecanoylphorbol-13-acetate concentration.

* * * * *